US007910627B2

(12) United States Patent
Toda et al.

(10) Patent No.: US 7,910,627 B2
(45) Date of Patent: Mar. 22, 2011

(54) NANOPARTICLE-DISPERSED HIGH-PERFORMANCE LIQUID FLUID, PRODUCTION METHOD AND APPARATUS FOR THE FLUID, AND LEAK DETECTION METHOD FOR THE FLUID

(75) Inventors: Mikio Toda, Tokyo (JP); Toshiro Nishi, Nagasaki-ken (JP); Nobuki Oka, Nagasaki-ken (JP); Hiroyuki Tsutaya, Nagasaki-ken (JP); Kuniaki Ara, Ibaraki (JP); Hiroaki Ohira, Ibaraki (JP); Kazuya Kurome, Hyogo-ken (JP); Naoki Yoshioka, Tokyo (JP)

(73) Assignee: Japan Nuclear Cycle Development Institute, Ibaraki (JP)

( * ) Notice: Subject to any disclaimer, the term of this patent is extended or adjusted under 35 U.S.C. 154(b) by 959 days.

(21) Appl. No.: 10/547,469

(22) PCT Filed: Jun. 16, 2005

(86) PCT No.: PCT/JP2005/011024
§ 371 (c)(1),
(2), (4) Date: Oct. 26, 2006

(87) PCT Pub. No.: WO2005/123869
PCT Pub. Date: Dec. 29, 2005

(65) Prior Publication Data
US 2007/0160177 A1  Jul. 12, 2007

(30) Foreign Application Priority Data
Jun. 16, 2004  (JP) .................................. 2004-178900

(51) Int. Cl.
*B01F 3/00* (2006.01)
*B01J 13/00* (2006.01)
(52) U.S. Cl. ............................. 516/9; 977/786; 977/787
(58) Field of Classification Search ...... 516/9; 977/786, 977/787
See application file for complete search history.

(56) References Cited

U.S. PATENT DOCUMENTS
2006/0037434 A1 * 2/2006 Bonnemann et al. ........... 75/348

FOREIGN PATENT DOCUMENTS
| DE | 102 06 083 A1 | | 8/2003 |
|---|---|---|---|
| DE | 10227779 A1 | * | 1/2004 |
| EP | 1 167 486 A1 | | 1/2002 |
| JP | 60-159625 | | 8/1985 |
| JP | 1-223324 | | 9/1989 |
| JP | 2003-249131 | | 9/2003 |
| JP | 10-2004-339461 | | 12/2004 |
| JP | 2004339461 A | * | 12/2004 |
| KR | 10-2004-0049921 | | 6/2004 |

OTHER PUBLICATIONS

H. Ohira and K. Ara, Investigation of Functional Liquid Metal With Dispersing Nanoparticles, JNC TN9400 2003-044 (Sep. 2003).*
Editors Association of Basic Fast Reactor Engineering: Basic Fast Reactor Engineering, published by Nikkan Kogyo Shimbun, Ltd., General Editor: Masao Hori, pp. 55-56, with English Translation 1993.
Hiroaki Ohira et al., "Investigation of functional liquid metal with dispersing nano-particles", Japan Nuclear Cycle Development Institute (with English abstract & partial English translation) 2003.
Hiroaki Ohira et al., "Development of functional liquid metal by dispersing nano-particles", The Japan Society of Mechanical Engineers 39th Autumn Lecture Meeting in Tohoku Branch, pp. 91-92 (with English translation) Sep. 5, 2003.

* cited by examiner

*Primary Examiner* — Glenn Caldarola
*Assistant Examiner* — Randy Boyer
(74) *Attorney, Agent, or Firm* — Oblon, Spivak, McClelland, Maier & Neustadt, L.L.P

(57) ABSTRACT

Suppression or enhancement of various properties of a liquid fluid is aimed by improving uniform dispersion of nanoparticles by means of making a state in which no oxidized film exists on the surfaces of the nanoparticles to be dispersed in the liquid fluid. The location of the liquid fluid is confirmed with ease by enhancing the brightness of light emission of the fluid through uniform dispersion of the nanoparticles in the liquid fluid containing a material having a flame reaction. In this way, as to liquid fluids utilized in various industries, it is possible to offer a technology to desirably enhance or suppress a property desired to be enhanced and a property desired to be suppressed among various properties that its constituents have.

8 Claims, 7 Drawing Sheets

EMISSION LUMINANCE OF D-LINE OF Na

NANOPARTICLE-DISPERSED HIGH-PERFORMANCE LIQUID FLUID, PRODUCTION METHOD AND APPARATUS FOR THE FLUID, AND LEAK DETECTION METHOD FOR THE FLUID

TECHNICAL FIELD

The present invention relates to a nanoparticle-dispersed high-performance liquid fluid containing a liquid fluid such as liquid sodium for cooling nuclear reactor as a base material, with which nanoparticles are mixed and dispersed therein for enhancing the performance of the liquid fluid. The present invention also relates to a production method of the liquid fluid, a production apparatus for the liquid fluid, and a leak detection method for liquid fluid.

BACKGROUND ART

As a liquid fluid used in various industries, there are a variety of liquid fluids beginning with, for example, liquid sodium for coolant for fast breeder reactor, a heat medium for heat exchanger that is arranged in various facilities, and an incompressible fluid for hydraulic machine. These liquid fluids have several properties specific to their materials. When judged from purpose of use, some properties are desired to be enhanced further, and some properties are desired to be suppressed further. For example, the liquid sodium for cooling has such an intense reactivity that an explosion occurs when it comes in contact with air or water.

Relation between a property specific to such a liquid fluid and a property desired in view of a purpose of use is further discussed below with an example of liquid sodium for cooling.

The reasons that sodium is used as a coolant for fast breeder reactor exist in excellent properties that liquid sodium has, for example; (i) a thermal conductivity of sodium is about 100 folds that of water, and sodium is capable of conducting heat effectively; (ii) sodium hardly moderates neutron and has good compatibility with nuclear reactor materials; (iii) sodium has a boiling point as high as about 880° C., and therefore, when thermal energy is converted into steam at a heat transfer end, it is possible to obtain steam with a temperature as high as about 480° C., resulting in that electric power generation with better thermal efficiency becomes possible; (iv) since the boiling point of sodium (about 880° C.) is higher than about 500° C. that is an operation temperature for fast breeder reactor, liquid sodium can be kept in liquid as it is without application of pressure and no high pressure is necessary to be applied to nuclear reactor and pipelines, and therefore, even if a sodium leak occurs, it does not blow out rapidly, and there is no fear to lose cooling capacity of the nuclear reactor (Non-patent document 1).

On the other hand, sodium has a property of such an intense reactivity that an explosion occurs when sodium comes in contact with air or water. However, in view of a purpose to utilize sodium as a coolant for fast breeder reactor, this property is a property that should be suppressed because there is a possibility that sodium comes in contact with air or water when it leaks from piping or the like.

Non-patent document 1: Kiso Kousokuro Kougaku Henshu Iinkai (edited): Kiso Kousokuro Kougaku, published by Nikkan Kogyo Shimbun, LTD (October, 1993).

DISCLOSURE OF INVENTION

Problem to be Solved by the Invention

As is described above, in various liquid fluids beginning with liquid sodium for a coolant for fast breeder reactor, there are some properties desired to be enhanced and some properties desired to be suppressed among various properties that the constituents of the liquid fluids have, and these properties coexist. When enhancement or suppression of these properties can be realized as desired, it is thought that a great contribution is provided to various industries. However, such a technology has not been realized so far.

The present invention was carried out in view of the circumstances described above, and the object of the present invention is to provide a technology in which, in liquid fluids being utilized in various industries, a property desired to be enhanced and a property desired to be suppressed among various properties that their constituents have are enhanced or suppressed as desired according to purposes of use (hereinafter, performance enhancement).

Means for Solving Problem

As a result of assiduous research to solve the problems, the present inventors obtained the following findings.

That is; (1) it was confirmed that when a ultrafine particle material in nanometer size (for example, nickel ultrafine particles) was mixed to be dispersed in a liquid fluid, for example, liquid sodium, changes in a flow property of the nanoparticle-dispersed liquid sodium that the reactivity to air and water was drastically reduced, the nanoparticle-dispersed liquid sodium had difficulty to pass through a narrow crevice like flaw of crack of piping or the like, and so forth occurred. Further, in other liquid fluids, changes such as reduction in toxicity and enhancement of heat conduction property occur.

Note that the constituent of the nanoparticle here is at least one kind selected from metals and nonmetals. Examples of the metals include single-element metals, such as copper (Cu), nickel (Ni), titanium (Ti), and cobalt (Co); their metallic compounds, such as oxides, nitrides, and suicides; and alloys, such as stainless steel and chrome molybdenum steel, and the like. Further, examples of the nonmetals include silicon, carbon, and the like. Nanoparticles can be obtained by crushing the metal or nonmetal into particles with a particle diameter of not larger than 1000 nm, preferably from 0.1 to 500 nm, and more preferably from 1 to 100 nm. In addition, there are materials currently commercially available as nanoparticles. For example, "nickel fine powder" "copper fine powder", and "cobalt fine powder" produced by Sumitomo Electric Industries, Ltd., "nickel metal nanopowder", "copper metal nanopowder", and "cobalt metal nanopowder" produced by Japan Nanotech Co. Ltd., and the like are available.

(2) Since some variations in these eminent effects were recognized at first, the present inventors further investigated through experiments with the aim of obtaining the effects stably and repeatedly. As the result, it was found that uniform dispersion of nanoparticles in a liquid fluid was required to enhance the reliability of the effects. In order to make this uniform dispersion possible, it was found that no formation of an oxidized film on the surface of the nanaoparticle was an important factor. When an oxidized film is present on the surface of the nanoparticle, its affinity for liquid sodium that is the base material (lyophilic property) is not excellent. Accordingly, even though nanoparticles are mixed while agitating the liquid sodium sufficiently, the nanoparticles partially aggregate in the liquid sodium, resulting in poor uniform dispersion. On the other hand, when the nanoparticles are converted to a state that oxidized films are not present on the surfaces thereof by removing or reducing the oxidized films, the affinity for the liquid sodium that is the base material becomes better. As the result, when the nanoparticles are mixed while agitating the liquid sodium, they are dispersed not only easily but also uniformly.

(3) Next, a specific method to realize a state in which the nanoparticles did not have oxidized films on their surfaces was investigated. First, it was found that, when broadly classified, (a) a method in which oxidized films were removed before the nanoparticles were mixed with liquid sodium, (b) a method to remove oxidized films while mixing, and (c) a method in which the surfaces of particles were covered with sodium atoms at the time of production of nanoparticles, in other words, a method in which the surface was covered with sodium atoms before formation of an oxidized film on the surface of the nanoparticle were realizable.

Specifically, the method (a) can be achieved by placing the nanoparticles having formed an oxide film under hydrogen gas atmosphere. Next, the method (b) can be achieved by mixing and agitating an oxygen getter before or after mixing nanoparticles in liquid sodium. The oxidized film is reduced during the agitating process. The last method (c) can be achieved by a novel apparatus. That is, it is possible to use a production apparatus composed of at least an evaporation chamber in which sodium and a material of the nanoparticles are vaporized and mixed under inert gas atmosphere; a molecular-beam chamber connected to the evaporation chamber via a small hole, in which the vaporized mixture inside the evaporation chamber issued from the small hole is received under vacuum atmosphere and a nanoparticle/sodium complex in a form where sodium atoms are adsorbed on the surfaces of the nanoparticles in the vaporized mixture is separated from other atomic sodium and nanoparticles depending on mass differences, and a collection chamber connected to the molecular-beam chamber, in which the separated nanoparticle/sodium complex is collected under vacuum atmosphere. With the manufacturing apparatus, nanoparticles with their surface covered with sodium atoms without surface oxide film can be obtained.

(4) After going through the series of the aforementioned experimental investigations, it was finally confirmed that another specific property a liquid fluid had was remarkably enhanced. There is a particular material that includes a constituent atom which emits light having a line spectrum upon application of a predetermined energy such as flame or electric discharge. It was observed that addition of nanoparticles to a liquid fluid containing at least the aforementioned particular material resulted in drastic increase in the brightness of the light having the line spectrum. For example, when nanoparticles were uniformly dispersed in liquid sodium under inert gas atmosphere, it was observed that emission of sodium D-line was enhanced in brightness as high as naked eyes could confirm when it was placed in the dark.

A light that naked eyes of human can recognize, so-called visible light is a light in a wavelength region of about from 400 nm to 800 nm, whereas the wavelength of emission of sodium D-line is 589.6 nm, and the emission can be recognized with naked eyes as a yellow light if it has a sufficient brightness. However, the emission of sodium D-line cannot be detected even by a photodetector, to say nothing of naked eyes because its brightness is extremely low unless excited by flame or electric discharge. As shown in FIG. 9, conventionally, to detect the presence or absence of a leak of liquid sodium from an opaque wall 1 of piping, container, and the like in a fast breeder reactor, laser beams were irradiated from tunable laser 3 to a generated gas (sodium gas) 2 at an inspection point to excite and amplify a faint emission of sodium D-line of the leaked sodium gas 2, and its excited atomic fluorescence 4 was condensed with a lens 5, thereby detecting it by a photodetector 6. In such a conventional leak detector, the photodetector 6 is composed of a spectroscope 6a and an image intensified charged couple device (ICCD) detector 6b. Timing of irradiating the tunable laser 3 and control of the shutter for opening/closing of the ICCD detector 6b are carried out by a controller 7. That is because the gas of inert gas atmosphere at the inspection point is excited by the laser irradiation with the tunable laser 3 to emit light, and the emission duration of this atmosphere gas and the duration of the atomic fluorescence 4 of the sodium gas 2 are different from each other. In other words, since the emission of the gas of the inert gas atmosphere after the laser irradiation decays in the first place, and the atomic fluorescence 4 of the sodium gas 2 decays later, opening the shutter of the ICCD detector 6b is necessary after the decay of the emission of the atmosphere gas.

On the other hand, when the brightness is enhanced to a level at which emission of sodium D-line can be detected by naked eyes only by means of dispersing the nanoparticles in the liquid sodium uniformly as described above, the use of tunable laser is not required, and no excitation of the gas of inert gas atmosphere is not accompanied, and therefore, it becomes possible to detect a gas leak easily with a leak detector in a simple structure including a photodetector and an optical system. Accordingly, when the nanoparticle-dispersed high-performance liquid fluid of the present invention is used in place of a conventional liquid fluid, it becomes possible to remarkably reduce a facility cost and a running cost for leak detection. This leads to easy confirmation of leak and location thereof (for example, moving velocity and spreading velocity) of not only liquid sodium for cooling but also any conventional liquid fluids, and benefits to industries in reduction in cost, acquisition of convenience, and the like that are associated with utilization of its properties become immense.

The present invention was carried out based on the findings described above.

In other words, the nanoparticle-dispersed high-performance liquid fluid according to a first exemplary embodiment of the present invention is a nanoparticle-dispersed high-performance liquid fluid enhanced in the performance by mixing and dispersing nanoparticles uniformly in a liquid fluid as the base material and is characterized in that no oxidized film is present on the surfaces of the nanoparticles in the liquid fluid base material, and the nanoparticles are uniformly dispersed in the liquid fluid base material.

The nanoparticle-dispersed high-performance liquid fluid of a second exemplary embodiment of the present invention is characterized in that the nanoparticle is at least one kind of ultrafine particle selected from a metal or a nonmetal in the nanoparticle-dispersed high-performance liquid fluid according to the first exemplary embodiment.

The nanoparticle-dispersed high-performance liquid fluid of third exemplary embodiment of the present invention is characterized in that a particle size of the nanoparticle is not larger than 1000 nm in diameter in the nanoparticle-dispersed high-performance liquid fluid according to the first exemplary embodiment.

The nanoparticle-dispersed high-performance liquid fluid of a fourth exemplary embodiment of the present invention is characterized in that the performance enhancement represents reduction in the specific reactivity possessed by the liquid fluid as the base material in the nanoparticle-dispersed high-performance liquid fluid according to the first exemplary embodiment.

The nanoparticle-dispersed high-performance liquid fluid of a fifth exemplary embodiment of the present invention is characterized in that the liquid fluid that is the base material is liquid sodium in the nanoparticle-dispersed high-performance liquid fluid according to the first exemplary embodiment.

The nanoparticle-dispersed high-performance liquid fluid of a sixth exemplary embodiment of the present invention is characterized in that the performance enhancement represents reduction in the reactivity to air or water possessed by the liquid sodium that is the base material in the nanoparticle-dispersed high-performance liquid fluid according to the fifth exemplary embodiment.

The nanoparticle-dispersed high-performance liquid fluid of a seventh exemplary embodiment of the present invention is characterized in that the performance enhancement represents reduction in minute-crack penetration property possessed by the liquid sodium that is the base material in the nanoparticle-dispersed high-performance liquid fluid according to the fifth exemplary embodiment.

The nanoparticle-dispersed high-performance liquid fluid of an eighth exemplary embodiment of the present invention is characterized in that the performance enhancement represents enhancement of the brightness of D-line emission specific to the liquid sodium that is the base material in the nanoparticle-dispersed high-performance liquid fluid according to the fifth exemplary embodiment.

A ninth exemplary embodiment of the present invention relates to a production method of a nanoparticle-dispersed high-performance liquid fluid, and this production method is characterized in that after nanoparticles are treated so as not to allow oxidized films to exist on the surfaces of the nanoparticles, the liquid fluid is enhanced in the performance by uniformly dispersing the nanoparticles in the liquid fluid.

The production method of nanoparticle-dispersed high-performance liquid fluid according to a tenth exemplary embodiment of the present invention is characterized in that removal of oxidized films on the surfaces of the nanoparticles is realized by placing the nanoparticles under hydrogen gas atmosphere for a predetermined time in the production method according to the ninth exemplary embodiment.

The production method of nanoparticle-dispersed high-performance liquid fluid according to an eleventh exemplary embodiment of the present invention is characterized in that the liquid fluid is enhanced in the performance by mixing nanoparticles with the liquid fluid, reducing the oxidized films on the surfaces of the nanoparticles at the same time, and dispersing the nanoparticles in the liquid fluid uniformly.

The production method of nanoparticle-dispersed high-performance liquid fluid according to a twelfth exemplary embodiment of the present invention is characterized in that the reduction of the oxidized films on the surfaces of the nanoparticles is realized by putting an oxygen getter into the liquid fluid before or after adding the nanoparticles in the liquid fluid in the production method according to the eleventh exemplary embodiment.

The production method of nanoparticle-dispersed high-performance liquid fluid according to a thirteenth exemplary embodiment of the present invention is characterized in that a material is used as the oxygen getter in the production method according to the twelfth exemplary embodiment, wherein the standard free energy of formation upon forming an oxide of the material is smaller than the standard free energy of formation upon forming oxides of other materials constituting the nanoparticles and the liquid fluid.

The production method of nanoparticle-dispersed high-performance liquid fluid according to a fourteenth exemplary embodiment of the present invention is characterized in that the material of the liquid fluid and the material of the nanoparticles are vaporized and mixed together under inert gas atmosphere, a nanoparticle/fluid atom complex in a form where constituting atoms of the material of the liquid fluid are adsorbed on the surfaces of the nanoparticles produced by the vaporization and mixing is separated from other atomic constituents of the liquid fluid and nanoparticles by means of issuing this vaporized mixture from a small hole under vacuum atmosphere depending on mass differences, and the separated nanoparticle/fluid atom complex is dispersed in the liquid fluid as the base material.

The production method of nanoparticle-dispersed high-performance liquid fluid according to a fifteenth exemplary embodiment of the present invention is characterized in that the nanoparticle is at least one kind of ultrafine particle selected from a metal or a nonmetal in the production method according to the ninth exemplary embodiment.

The production method of nanoparticle-dispersed high-performance liquid fluid according to a sixteenth exemplary embodiment of the present invention is characterized in that the nanoparticle is at least one kind of ultrafine particle selected from a metal or a nonmetal in the production method according to the eleventh exemplary embodiment.

The production method of nanoparticle-dispersed high-performance liquid fluid according to a seventeenth exemplary embodiment of the present invention is characterized in that the nanoparticle is at least one kind of ultrafine particle selected from a metal or a nonmetal in the production method according to the fourteenth exemplary embodiment.

The production method of nanoparticle-dispersed high-performance liquid fluid according to an eighteenth exemplary embodiment of the present invention is characterized in that the particle size of the nanoparticle is not larger than 1000 nm in diameter in the production method according to the ninth exemplary embodiment.

The production method of nanoparticle-dispersed high-performance liquid fluid according to a nineteenth exemplary embodiment of the present invention is characterized in that the particle size of the nanoparticle is not larger than 1000 nm in diameter in the production method according to the eleventh exemplary embodiment.

The production method of nanoparticle-dispersed high-performance liquid fluid according to a twentieth exemplary embodiment of the present invention is characterized in that the particle size of the nanoparticle is not larger than 1000 nm in diameter in the production method according to the fourteenth exemplary embodiment.

The production method of nanoparticle-dispersed high-performance liquid fluid according to a twenty-first exemplary embodiment of the present invention is characterized in that the performance enhancement represents reduction in a specific reactivity possessed by the liquid fluid as the base material in the production method according to the ninth exemplary embodiment.

The production method of nanoparticle-dispersed high-performance liquid fluid according to a twenty-second exemplary embodiment of the present invention is characterized in that the performance enhancement represents reduction in the specific reactivity possessed by the liquid fluid as the base material in the production method according to the eleventh exemplary embodiment.

The production method of nanoparticle-dispersed high-performance liquid fluid according to a twenty-third exemplary embodiment of the present invention is characterized in that the performance enhancement represents reduction in the specific reactivity possessed by the liquid fluid as the base material in the production method according to the fourteenth exemplary embodiment.

The production method of nanoparticle-dispersed high-performance liquid fluid according to a twenty-fourth exemplary embodiment of the present invention is characterized in that the liquid fluid that is the base material is liquid sodium in the production method according to the ninth exemplary embodiment.

The production method of nanoparticle-dispersed high-performance liquid fluid according to a twenty-fifth exemplary embodiment of the present invention is characterized in that the liquid fluid that is the base material is liquid sodium in the production method according to the eleventh exemplary embodiment.

The production method of nanoparticle-dispersed high-performance liquid fluid according to a twenty-sixth exemplary embodiment of the present invention is characterized in that the liquid fluid that is the base material is liquid sodium in the production method according to the fourteenth exemplary embodiment.

The production method of nanoparticle-dispersed high-performance liquid fluid according to a twenty-seventh exemplary embodiment of the present invention is characterized in that the performance enhancement represents reduction in reactivity to air or water possessed by the liquid sodium that is the base material in the production method according any one of the twenty-fourth, twenty-fifth and twenty-sixth exemplary embodiments.

The production method of nanoparticle-dispersed high-performance liquid fluid according to a twenty-eighth exemplary embodiment of the present invention is characterized in that the performance enhancement represents reduction in minute-crack penetration property possessed by the liquid sodium that is the base material in the production method according to any one of the twenty-fourth, twenty-fifth and twenty-sixth exemplary embodiments.

The production method of nanoparticle-dispersed high-performance liquid fluid according to a twenty-ninth exemplary embodiment of the present invention is characterized in that the performance enhancement represents enhancement of the brightness of D-line emission specific to the liquid sodium that is the base material in the production method according to any one of the twenty-fourth, twenty-fifth and twenty-sixth exemplary embodiments.

A thirtieth exemplary embodiment of the present invention relates to a production apparatus for nanoparticle-dispersed high-performance liquid fluid, and this production apparatus is a production apparatus for a nanoparticle-dispersed high-performance liquid fluid enhanced in the performance by mixing and dispersing nanoparticles in a liquid fluid as the base material, and is characterized in at least having: an evaporation chamber in which the material of the liquid fluid and the material of the nanoparticles are vaporized and mixed under inert gas atmosphere; a molecular-beam chamber connected to the evaporation chamber via a small hole, in which the vaporized mixture inside the evaporation chamber issued from the small hole is received under vacuum atmosphere, and "the nanoparticle/liquid fluid constituting atom complex in a form where constituting atoms of the liquid fluid material are adsorbed on the surfaces of the nanoparticles (hereinafter, nanoparticle/fluid atom complex)" formed in the vaporized mixture is separated from other atomic constituents of the liquid fluid and nanoparticles depending on mass differences; and a collection chamber connected to the molecular-beam chamber, in which the separated nanoparticle/fluid atom complex is collected under vacuum atmosphere.

The production apparatus for nanoparticle-dispersed high-performance liquid fluid according to a thirty-first exemplary embodiment of the present invention is characterized in that a uniform mixing unit to mix and disperse the nanoparticle/fluid atom complex in the liquid fluid is provided in the downstream of the collection chamber in the production apparatus according to the thirtieth exemplary embodiment.

The production apparatus for nanoparticle-dispersed high-performance liquid fluid according to a thirty-second exemplary embodiment of the present invention is characterized in that the nanoparticle is at least one kind of ultrafine particle selected from a metal or a nonmetal in the production apparatus according to the thirtieth exemplary embodiment.

The production apparatus for nanoparticle-dispersed high-performance liquid fluid according to a thirty-third exemplary embodiment of the present invention is characterized in that the size of the nanoparticle is formed so as to be not larger than 1000 nm in diameter in the production apparatus according to the thirtieth exemplary embodiment.

The production apparatus for nanoparticle-dispersed high-performance liquid fluid according to a thirty-fourth exemplary embodiment of the present invention is characterized in that the performance enhancement represents reduction in a specific reactivity possessed by the liquid fluid as the base material in the production apparatus according to the thirtieth exemplary embodiment.

The production apparatus for nanoparticle-dispersed high-performance liquid fluid according to a thirty-fifth exemplary embodiment of the present invention is characterized in that the liquid fluid that is the base material is liquid sodium in the production apparatus according to the thirtieth exemplary embodiment.

The production apparatus for nanoparticle-dispersed high-performance liquid fluid according to a thirty-sixth exemplary embodiment of the present invention is characterized in that the performance enhancement represents reduction in the reactivity to air or water possessed by the liquid sodium that is the base material in the production apparatus according to the thirty-fifth exemplary embodiment.

The production apparatus for nanoparticle-dispersed high-performance liquid fluid according to a thirty-seventh exemplary embodiment of the present invention is characterized in that the performance enhancement represents reduction in the minute-crack penetration property possessed by the liquid sodium that is the base material in the production apparatus according to the thirty-fifth exemplary embodiment.

The production apparatus for nanoparticle-dispersed high-performance liquid fluid according to a thirty-eighth exemplary embodiment of the present invention is characterized in that the performance enhancement represents enhancement of the brightness of D-line emission specific to the liquid sodium that is the base material in the production apparatus according to the thirty-fifth exemplary embodiment.

A thirty-ninth exemplary embodiment of the present invention relates to a leak detection method for liquid fluid, and this leak detection method is characterized in that a leak is detected easily and promptly by dispersing nanoparticles uniformly in a liquid fluid containing at least a material having a flame reaction to enhance the brightness of light emission of the liquid fluid and detecting the light emission enhanced in brightness of the leaked liquid fluid when the liquid fluid leaks through an opaque wall.

The leak detection method for liquid fluid according to a fortieth exemplary embodiment of the present invention is characterized in that the liquid fluid is liquid sodium in the leak detection method according to the thirty-ninth exemplary embodiment.

EFFECTS OF THE INVENTION

The nanoparticle-dispersed liquid fluid of the present invention is a nanoparticle-dispersed high-performance liquid fluid enhanced in the performance by mixing and dispersing nanoparticles uniformly in a liquid fluid as the base material and is characterized in that no oxidized film exists on the surfaces of the nanoparticles in the liquid fluid base material, and the nanoparticles are dispersed in the liquid fluid base material uniformly. Owing to such a composition, it becomes possible to desirably enhance or suppress a property desired to be enhanced and a property desired to be suppressed further among various specific properties possessed by a liquid fluid according to the purpose of use. Therefore, according to the present invention, since an alternative liquid fluid with high performance can be provided at low cost only by mixing nanoparticles in a liquid fluid conventionally used in various industrial fields in a state where no oxidized film exists on the surfaces of the nanoparticles, followed by dispersing them uniformly, its application effect on industries is enormous. Particularly, when the nanoparticles are applied to a liquid fluid having an emission property, the brightness of the light emission can be significantly increased, which makes it possible to obtain significant effects that detection of a leak of the liquid fluid, confirmation of its location (measurement of moving velocity, dispersion velocity and the like), and the like become easy.

EXPLANATIONS OF LETTERS AND NUMERALS

Figure 1:
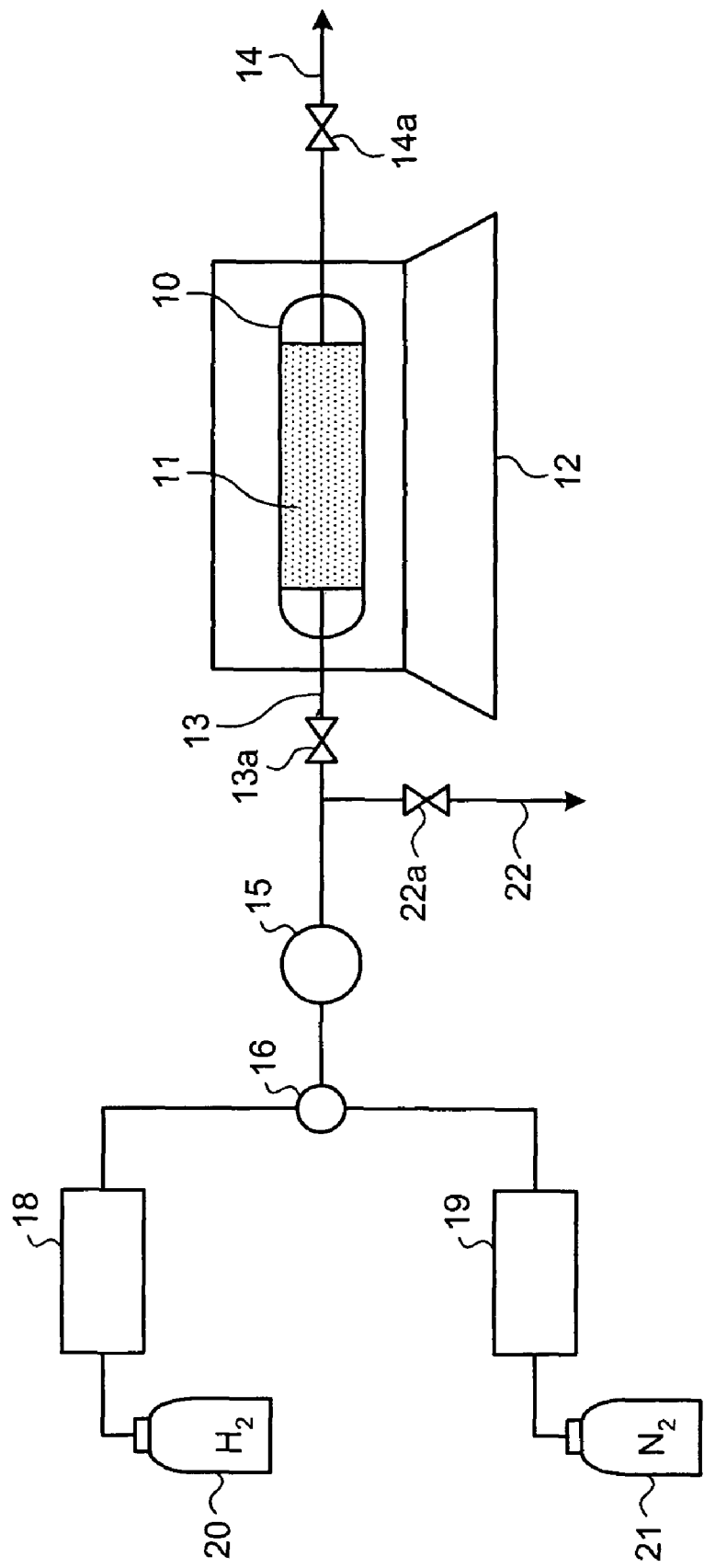
FIG. 1 is a diagram to explain a first embodiment of the present invention and is a schematic structural diagram of an apparatus of hydrogen reduction to reduce oxidized films on the surfaces of nanoparticles.

1. Opaque wall
2. Leaked liquid sodium
3. Tunable laser
4. Photodetector
10. Glass tube
11. Nanoparticles
12. Gold furnace
13. Gas inflow pipe
13a. Open/close valve
14. Gas outflow pipe
14a. Open/close valve
15. Flowmeter
16. Mixer
18. 19, Mass flow controller
20. Hydrogen tank
21. Nitrogen tank
22. Branch pipe
22a. Open/Close valve
30. Crucible
31. Mantle heater
32. Liquid sodium
33. Stirrer device
33a. Stirrer propeller
34. Thermocouple
35. Aluminum wire (oxygen getter)
40. Evaporation chamber
41. Molecular-beam chamber
42. Collection chamber
43. Small hole
44. Vaporized mixture
45. Nanoparticle/fluid atom complex
46. Atomic material
47. Opening/closing unit
48. Sodium metal bar
49. Nickel bar
50, 51. Pulse laser beam
52. Molecular beam
53, 54. Skimmer
55, 56, 57. Siphon
58. Collection plate
60. Emission area
70. Nanoparticle-dispersed high-performance liquid sodium
71. Emission
72. Condenser lens
73. Simple photodetector

MODE FOR CARRYING OUT THE INVENTION

Hereinafter, embodiments of the present invention are explained in detail based on the accompanying drawings. Note that the embodiments explained below are mere examples to explain the present invention exemplarily and do not limit the present invention at all.

First Embodiment

FIG. 1 is a schematic structural diagram of an apparatus of hydrogen reduction of nanoparticles to obtain "nanoparticles that do not have oxidized films on the surfaces" constituting a nanoparticle-dispersed high-performance liquid fluid of the present invention. The numeral 10 in the figure represents a glass tube to put in nanoparticles 11, and this glass tube 10 is fixed to a gold furnace 12. To the glass tube 10, a gas inflow pipe 13 and a gas outflow pipe 14 are connected, and open/ close valves 13a and 14a are placed in the flow of each of the pipes 13 and 14, respectively. A flowmeter 15 is arranged in the upstream of the gas inflow pipe 13, and a gas mixer 16 is connected in the further upstream thereof. Two gas pipes are connected to the mixer 16, and mass flow controllers 18 and 19 are attached to both of the two gas pipes, respectively. A hydrogen gas tank 20 is connected to one of the pipes and a nitrogen gas tank 21 is connected to the other pipe. The glass tube 10 can be detached in a hermetic state from the flow path by means of stoppers not shown. The numeral 22 in the figure represents a branch pipe, and an open/close valve 22a is attached to this branch pipe 22. Degassing of the pipe system is possible by opening the open/close valve 22a.

Reduction processing for oxidized films on the surfaces of nanoparticles by the apparatus of hydrogen reduction is carried out as follow. First, nanoparticles on which oxidized films have been formed on the surfacesare put in the glass tube 10. The open/close valves 13a and 14a are opened, the stoppers of the hydrogen tank 20 and the nitrogen tank 21 are opened, respectively, and each of the mass flow controllers 18 and 19 is adjusted to prepare a hydrogen-nitrogen mixed gas at a desired ratio in the mixer 16. This mixed gas is supplied to the glass tube 10 at a predetermined flow rate while monitoring with the flowmeter 15. The nanoparticles 11 in the glass tube 10 are exposed to the hydrogen-nitrogen mixed gas at the predetermined flow rate, and the oxidized films on the surfaces are reduced to give nanoparticles free from oxidized films on the surfaces. After a reduction time set experientially has passed, not only the open/close valve 22a for degassing is opened but also the open/close valve 14a is closed, and then the open/close valve 13a is closed. Then, the glass tube 10 is made hermetic with the use of the stoppers not shown to be detached from the gas flow path, and it is transferred to a process of dispersion in a liquid fluid such as liquid sodium.

A specific example of hydrogen reduction conditions by the apparatus of hydrogen reduction includes that, when a hydrogen concentration is 10%, a treatment temperature is 180° C., a gas flow rate is from 100 to 200 mL/min, and treatment time is from 6 to 60 seconds to carry out reduction processing of 0.1 g of nanoparticles.

In the process of dispersion in the liquid fluid, the nanoparticles are poured from the glass tube 10 into the liquid fluid filled in a container such as crucible while agitating the liquid fluid. A desired effect can be obtained in a mixing content of the nanoparticles in the liquid fluid at at least 10 parts per million (ppm). Preferably a mixing at 50 ppm is good and a mixing at 100 ppm is quite sufficient. The nanoparticles have been treated to a state without any oxidized films on the surfaces in the hydrogen reduction processing, and therefore, the affinity for a liquid fluid is high, and the nanoparticles are easy to be mixed and dispersed uniformly. To make this uniform dispersion better, it is preferred that the particle distribution of the nanoparticles is as narrow as possible.

Second Embodiment

Figure 2:
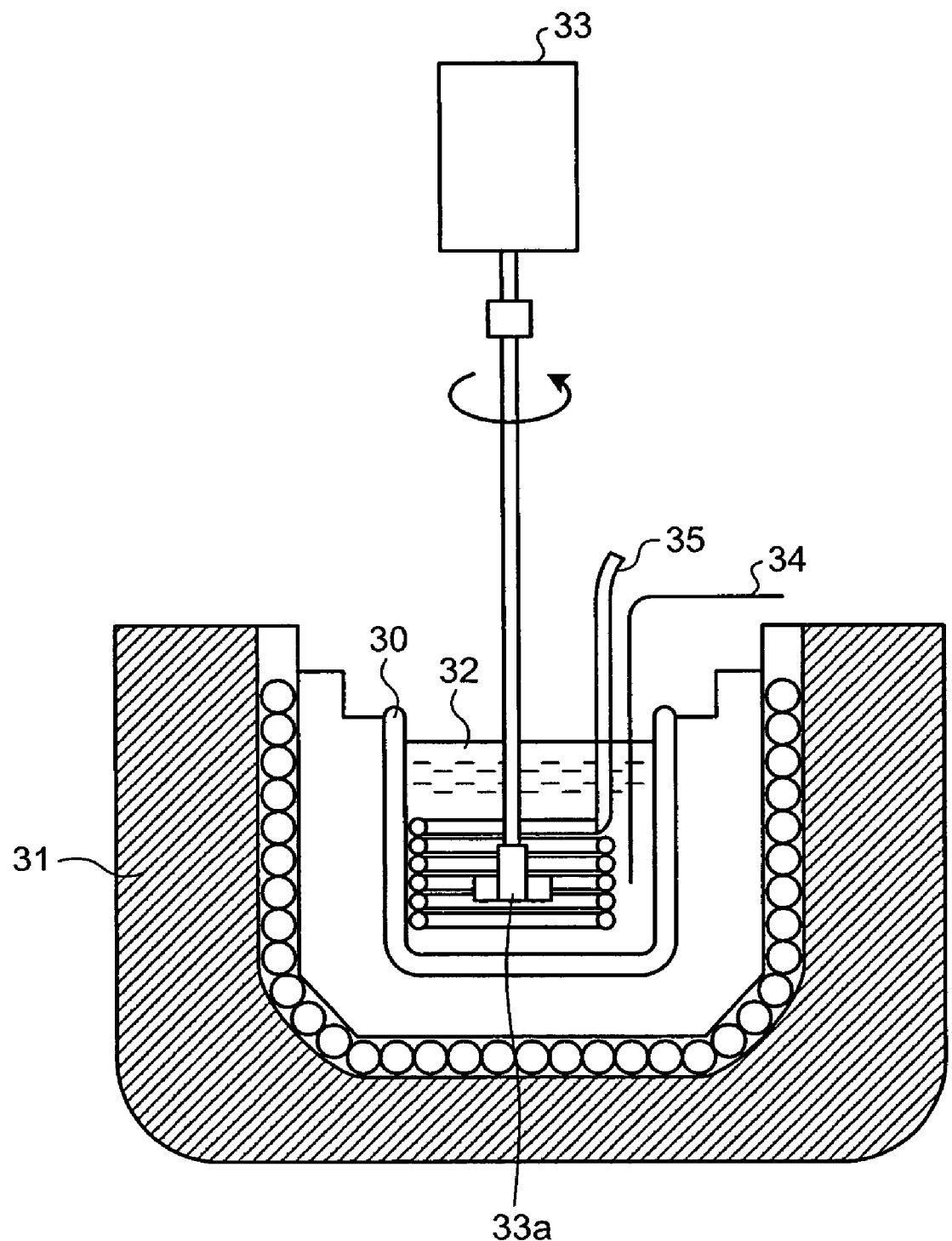
FIG. 2 is a diagram to explain a second embodiment of the present invention and is a schematic structural diagram of a production apparatus for nanoparticle-dispersed high-performance liquid fluid that carries out reduction of oxidized films on the surfaces of nanoparticles and uniform dispersion of the nanoparticles in a liquid fluid at the same time.

FIG. 2 represents an example of a production apparatus for nanoparticle-dispersed high-performance liquid fluid in a laboratory scale. This production apparatus is an apparatus in a case where liquid sodium is used as a liquid fluid.

The numeral 30 in the figure represents a ceramic crucible arranged in a mantle heater 31, and liquid sodium 32 is filled in its inside, kept at from 250° C. to 350° C., and placed under an inert gas. In the approximate center of the crucible 30, a stirrer propeller 33a of a stirrer device 33 is inserted, and a thermocouple 34 for temperature measurement is inserted near the sidewall. Further, an aluminum wire 35 formed in a spiral fashion along the inner wall is arranged in the crucible 30 as an oxygen getter.

The removal of the oxidized films on the surfaces of the nanoparticles by the production apparatus for nanoparticle-dispersed high-performance liquid fluid in the structure and simultaneous production of a nanoparticle-dispersed high-performance liquid fluid are carried out as follow.

Figure 3:
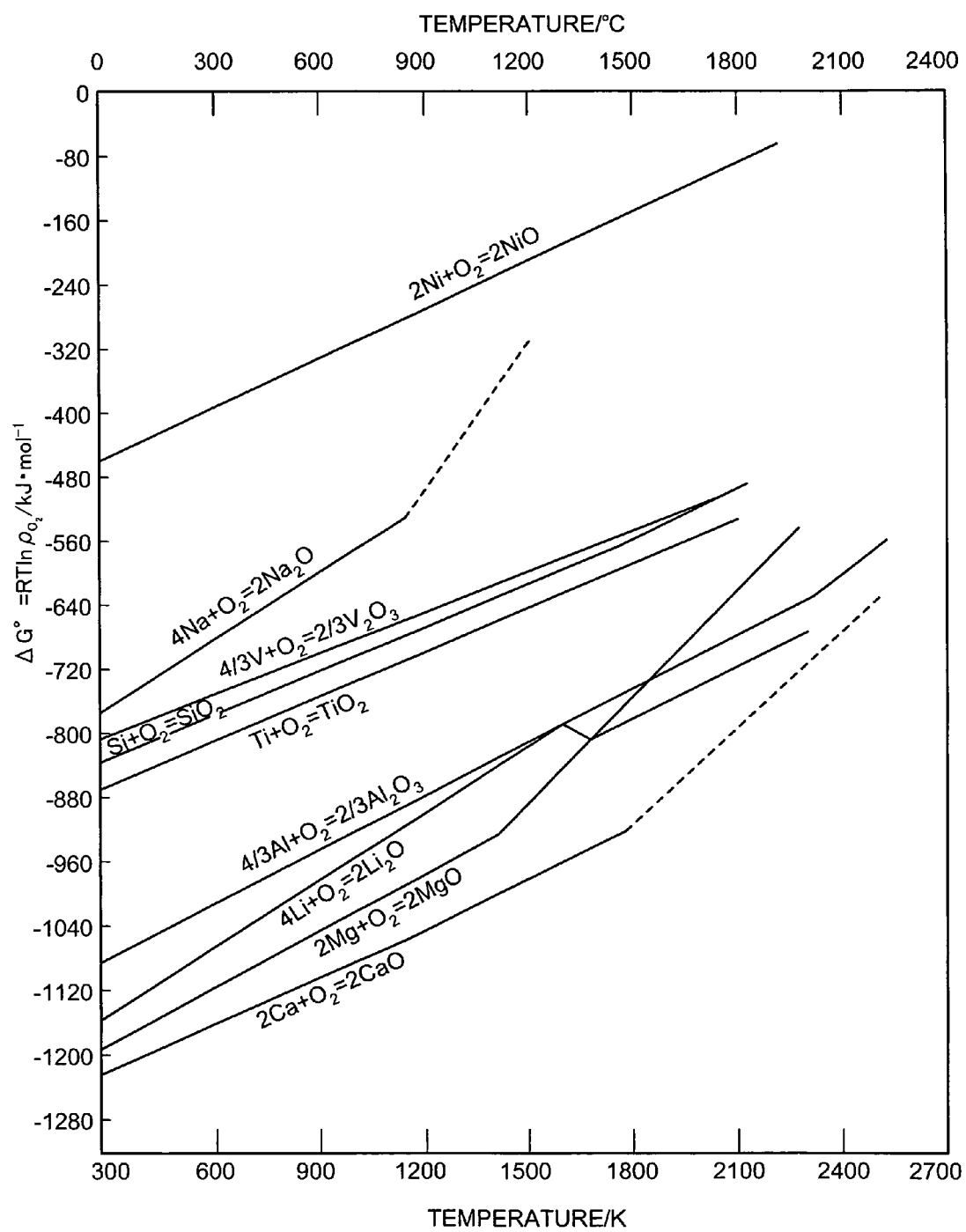
FIG. 3 is a graph of standard free energy of formation/temperature for oxide formation that becomes a standard when an oxygen getter essentially used for the production apparatus shown in FIG. 2 is selected.

For example, nickel ultrafine particles are used as the nanoparticles. Since oxidized films have already been generally formed immediately after these nickel ultrafine particles are produced, the nickel ultrafine particles are used on the precondition that oxidized films on the surfaces exist. These nanoparticles are gradually added to the liquid sodium 32 inside the crucible 30 until they become from 20 to 30 mass percent (%) of the whole amount of sodium (it is an excess amount but the uniform dispersion concentration finally settles to from 10 to 100 ppm. The excess particles precipitate.) During the addition, the stirrer propeller 33a is rotated at all times to agitate the liquid sodium 32 sufficiently. Since the standard free energy of formation when the oxide of aluminum constituting the aluminum wire 35 is produced is lower than that of sodium and nickel as shown by the graph in FIG. 3, oxygen bound to nickel is liberated from the nickel to come to bind to aluminum. As the result, the oxidized films on the surfaces of the nickel ultrafine particles are reduced, leading to a state in which no oxidized film exists on the surfaces of the nickel ultrafine particles. The nickel ultrafine particles without any oxidized film on the surfaces have a good affinity for the liquid sodium 32, and therefore become easily dispersed and distributed in the liquid sodium 32 uniformly. To be more precise, sampling is carried out with the use of a sampling tube made of stainless steel not shown or the like, and the temperature of the sample is lowered to observe the section of the solidified block, which makes it possible to confirm the uniform distribution by observing whether there are any precipitates or aggregates of the nickel ultrafine particles.

In this way, an oxygen getter is put in the liquid fluid in advance, and uniform dispersion of the nanoparticles is aimed while removing oxidized films on the surfaces of the nanoparticles by mixing the nanoparticles while agitating the liquid fluid, and therefore, there is an advantage that a nanoparticle-dispersed high-performance liquid fluid can be effectively produced.

Note that, in this second embodiment, the aluminum wire (oxygen getter) is arranged in advance in the liquid sodium filled in the crucible, however, even if the aluminum wire is put in after beginning to add and mix the nickel ultrafine particles, a similar effect can be obtained.

Third Embodiment

Figure 4:
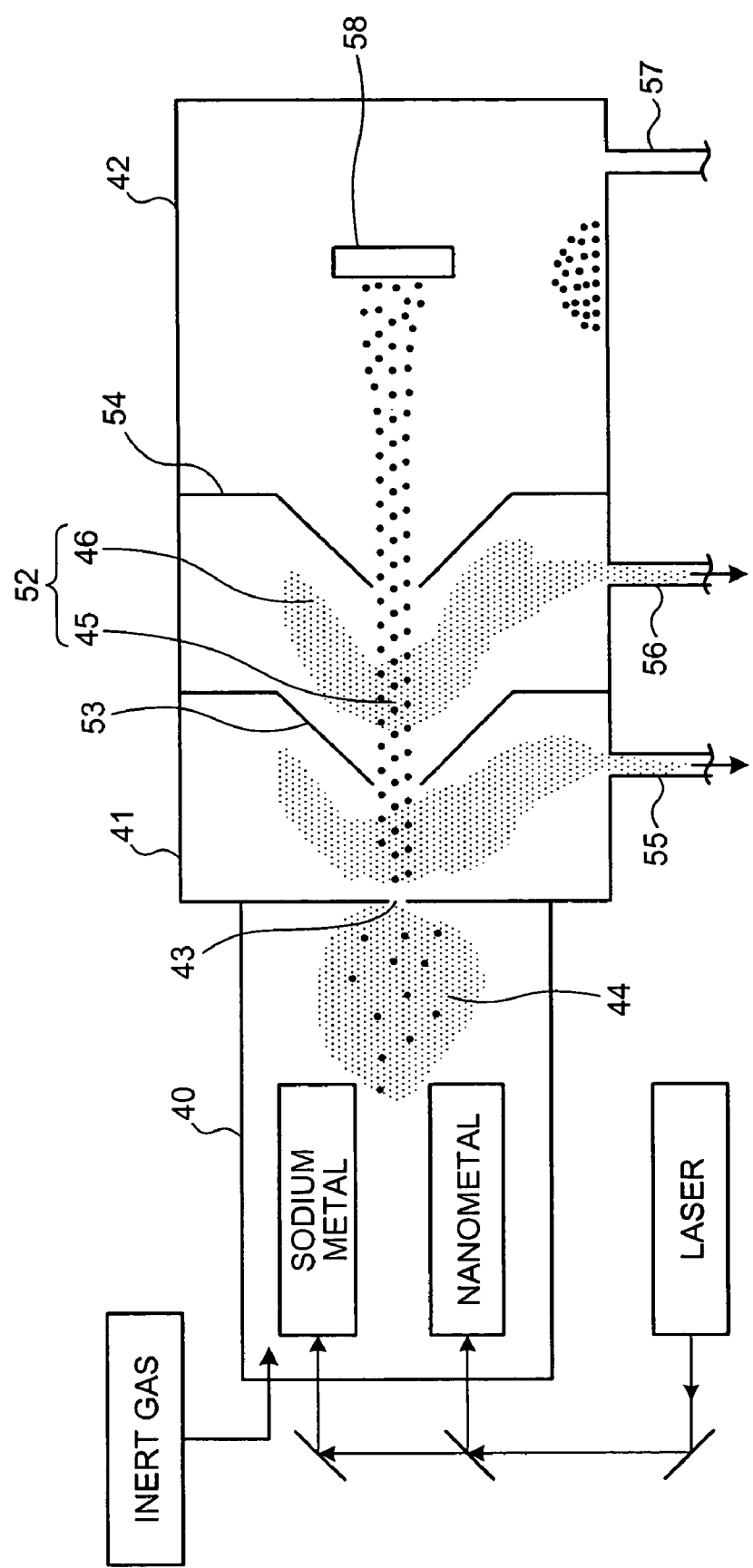
FIG. 4 is a diagram to explain a third embodiment of the present invention and is a schematic structural diagram of a production apparatus for nanoparticle-dispersed high-performance liquid fluid, characterized in that production of nanoparticles and bonding of atoms of the material constituting a liquid fluid that is the base material to the surfaces of the formed nanoparticles are carried out at the same time.
Figure 5:
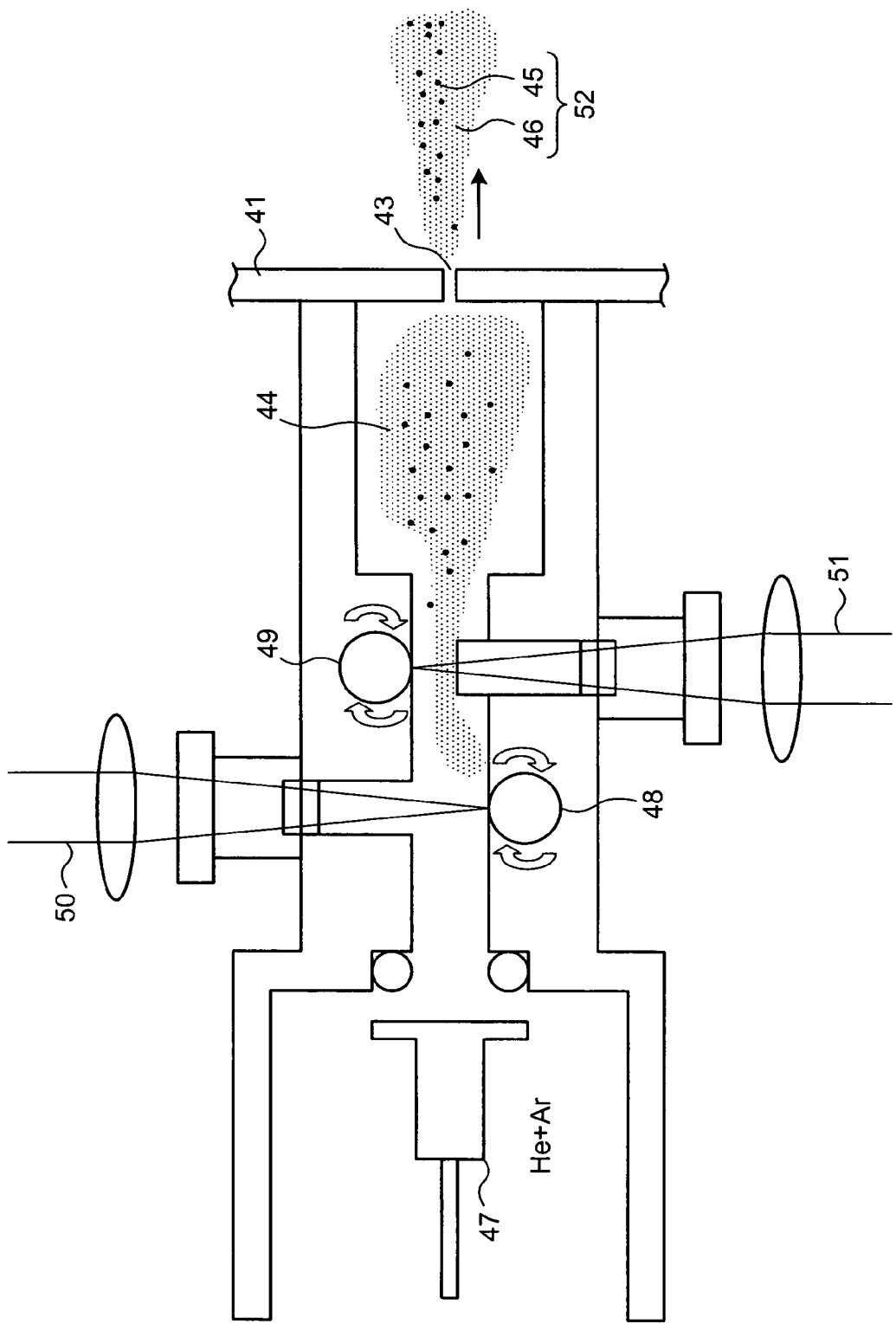
FIG. 5 is a detailed structural diagram of an evaporation chamber constituting part of the production apparatus shown in FIG. 4.

FIG. 4 and FIG. 5 represent another embodiment of the production apparatus for nanoparticle-dispersed high-performance liquid fluid. This production apparatus is composed of an evaporation chamber 40, a molecular-beam chamber 41, and a collection chamber 42 that are sequentially connected to each other.

The evaporation chamber 41 is a chamber where a material serving as a liquid fluid (e.g. sodium) and a material serving as nanoparticles (e.g. nickel) are vaporized and mixed under inert gas atmosphere.

The molecular-beam chamber 41 is a chamber connected to the evaporation chamber 40 via a small hole 43, in which a vaporized mixture 44 inside the evaporation chamber 40 issued from the small hole 43 is received under vacuum atmosphere, and "the nanoparticle/liquid fluid constituting atom complex in a form where constituting atoms of the liquid fluid material are adsorbed on the surfaces of the nanoparticles (hereinafter, nanoparticle/fluid atom complex)" 45 formed in the vaporized mixture is separated from other atomic constituents of the liquid fluid and nanoparticles 46 depending on mass differences.

The collection chamber 42 is a chamber connected to the molecular-beam chamber 41, in which the separated nanoparticle/fluid atom complex 45 is collected under vacuum atmosphere.

A further detailed structure of the evaporation chamber 40 is shown in FIG. 5. An opening/closing unit 47 is arranged on the side opposite to the small hole 43 of the chamber 40, and an inert gas such as helium (He)+argon (Ar) mixed gas is introduced into the inside of the chamber 40. In addition, in the chamber 40, blocks of the constituents of the liquid fluid, for example, a sodium metal bar 48 and a block of the constituent of the nanoparticles, for example, a nickel bar 49 can be rotatably arranged. To the sodium metal bar 48 and the nickel bar 49, pulse laser beams 50 and 51 can be irradiated from outside, respectively.

In the chamber 40 in the described structure, two kinds of metal rods (the sodium metal bar 48 and the nickel bar 49) desired to be mixed are vaporized by irradiation of the pulse laser beams 50 and 51. A He+Ar mixed gas is issued as a carrier gas from the small hole 43 to the vacuum atmosphere in the adjacent molecular chamber 41 to form a molecular beam 52. In such a laser vaporization method, it is possible to vaporize a target metal even though its melting point is fairly high, which is advantageous. As the described pulse laser beams 50 and 51, for example, second harmonic YAG laser (wave length of 532 nm, output of 300 mJ) such as copper vapor laser is used, and laser beams are allowed to be condensed with a condenser lens. When a metal is vaporized with the use of pulse laser, the molecular beam 52 is generally generated in a pulse form to reduce load of an exhauster of a vacuum system. In the molecular beam 52, the atomic metals 46 resulted from vaporization of each metal and the nanoparticle/fluid atom complex 45 in a state (molecular state) where sodium atoms are adsorbed on the surfaces of the nanoparticles (nickel ultrafine particles) are mixed.

In the described vacuum chamber 41, skimmers 53 and 54 are sequentially arranged along the flow direction of the molecular beam 52, and the vacuum chamber 41 is partitioned into two chambers by these skimmers 53 and 54. To each partitioned chamber, siphons 55 and 56 connected to vacuum pumps not shown are connected, respectively. The atomic materials in the molecular beam 52 are captured in each chamber by these skimmers 53 and 54 and discharged from the siphons to the outside of the system. The rest of the nanoparticle/fluid atom complex 45 is flown to the adjacent collection chamber 42 without being captured by the skimmers 53 and 53.

The collection chamber 42 is connected to a siphon 57 which are similarly connected to a non-shown vacuum pump, and the inside of the chamber is under vacuum atmosphere. In this collection chamber 42, a collection plate 58 is arranged so as to obstruct the molecular beam 52 perpendicularly. Most molecular beam 52 reaching here is practically composed of the nanoparticle/fluid atom complex 45. The fast-speed flow of the complex 45 collides against the collection plate 58 and the complex 45 accumulates in the chamber 42.

The nanoparticle/fluid atom complex 45 prepared and collected as described above has become particles in a state where sodium atoms are adsorbed on the surfaces of the nanoparticles (nickel ultrafine particles) or aggregates (cluster), and the surface portions are covered with sodium, and therefore, when the particles or the aggregates are added to liquid sodium that is the base material of the liquid fluid and then agitated, they are mixed with ease and become in a state of uniform dispersion instantly. According to the apparatus and the production method of this embodiment, making a nanoparticle and protection of its surface can be carried out at the same time. Thus, an oxidized film is not formed. In addition, since the atoms protecting the surface are atoms of the constituents of the liquid fluid, the affinity of the obtained complex particles or cluster for the liquid fluid that is the base material becomes very high. Accordingly, it is possible to produce a nanoparticle-dispersed high-performance liquid fluid of high quality at low cost.

Typical properties that are performance enhanced in the nanoparticle-dispersed high-performance liquid fluid prepared according to the three described methods for removing oxidized films on the surfaces are briefly explained below. It is judged that the effect of enhanced properties results from sufficient removal of the oxidized films by the removing unit for oxidized film specific to the present invention and highly uniform dispersion of the nanoparticles in the liquid fluid.

First, as the performance enhancement confirmed from the beginning of the research, the following items can be listed.

(1) When the nanoparticle-dispersed high-performance liquid fluid used in the piping or the container leaks, the virtual leak volume of the liquid fluid that is the base material becomes less by the volume occupied by the nanoparticles compared to a conventional liquid fluid, assuming that the leak volume containing the nanoparticles and the leak volume without containing the nanoparticles are equal to each other, and therefore, the reactivity or toxicity possessed by the liquid fluid itself that is the base material is reduced.

(2) When cracking occurs in the piping, the container, or the like, the uniformly dispersing nanoparticles serve as a flow resistance for the liquid fluid that is the base material, and therefore, the leak volume is significantly reduced compared to that of a conventional liquid fluid.

(3) Since the liquid fluid that is the base material is trapped in layers on the outer peripheral surfaces of the nanoparticles that have been uniformly dispersed in the nanoparticle-dispersed high-performance liquid fluid, emergence of the reactivity of the liquid fluid that is the base material can be comparatively delayed.

(4) It becomes possible to enhance the heat transfer property significantly compared to the conventional heat transfer medium by selecting ultrafine metal particles having a thermal conductivity suitable for nanoparticles and uniformly dispersing them in a liquid fluid that is a heat transfer medium for a conventional heat exchanger.

When the present inventors further studied through investigation on the properties of the nanoparticle-dispersed high-performance liquid fluid having excellently high uniform dispersion obtained by the present invention, they could find with a surprise that a property change seemingly adverse to the reduction in the reactivity as described above occurred.

Figure 6:
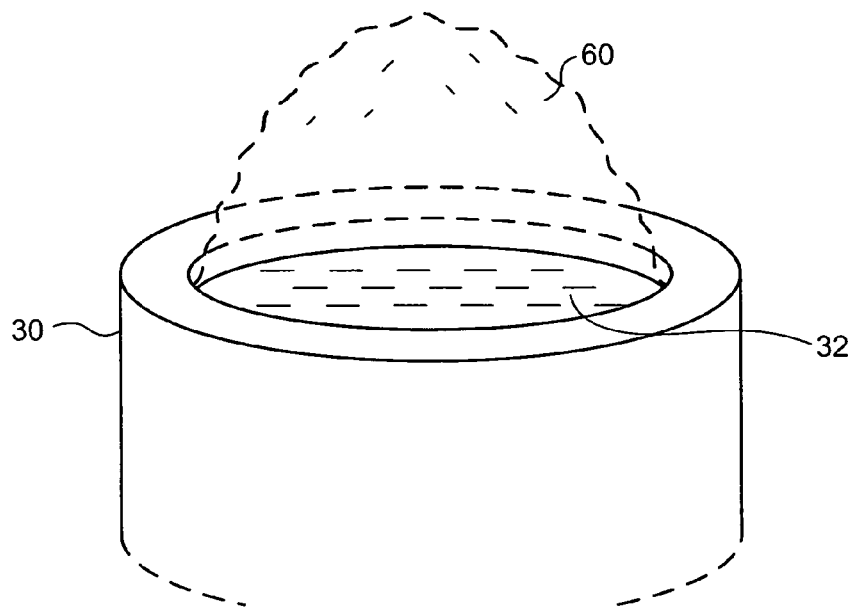
FIG. 6 is a diagram to explain enhancement in brightness of light emission property in the nanoparticle-dispersed high-performance liquid fluid of the present invention and is a perspective view representing a state where the nanoparticle-dispersed high-performance liquid fluid in a crucible is emitting.

Specifically, this change was confirmed in the middle of the process in which the liquid sodium 32 as the base material was filled in the crucible 30 as shown in FIG. 6 and subjected to agitating operation under heating so as to uniformly disperse nickel ultrafine particles as nanoparicles in this base material. It was confirmed that, when the environment was made dark in a state that the nanoparticles were uniformly dispersed in the crucible 30 heated under inert gas atmosphere, the liquid sodium in the crucible 30 emitted light with a brightness as high as naked eyes could recognize. Since liquid sodium without being mixed with the nanoparticles did not have a brightness as high as naked eyes could confirm as described hereinbefore in FIG. 9, a leak of liquid sodium from the piping could not be detected even by a photodetector unless emission of sodium D-line was excited by making use of a tunable laser system that was troublesome in maintenance and occupied a large space. However, only by dispersing the nanoparticles uniformly, the brightness of liquid sodium is enhanced as high as naked eyes can confirm.

Figure 7:
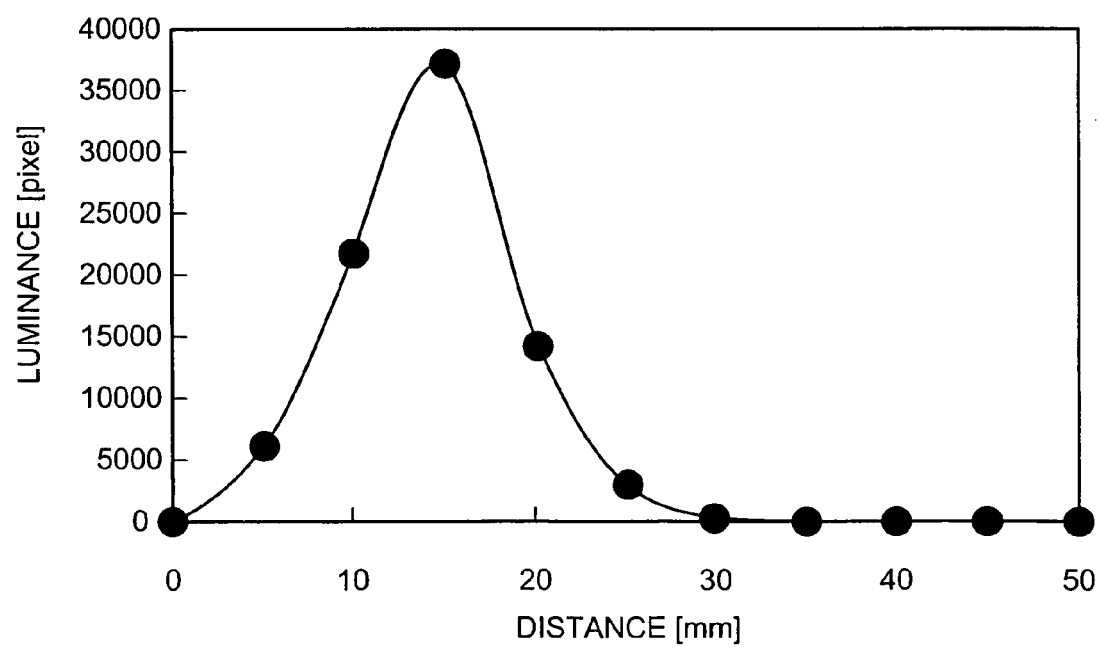
FIG. 7 is a graph representing the light-emission brightness determined from images obtained by imaging the emission area shown in FIG. 6.

The present inventors placed the crucible 30 in the dark environment and imaged an emission area 60 and its adjacent area in a flame form from the nanoparticle-dispersed high-performance flow fluid in the crucible 30 with a CCD imaging device. The brightness of the pixels on its picture image was analyzed and digitalized, thereby making a graph by plotting with the distance from the center of the flame-like emission area on the horizontal axis and the brightness of the light emission on the vertical axis. The graph was shown in FIG. 7. This graph shows the number of pixels as a measure of the brightness of the light emission. Even though the brightness in a case of only conventional liquid sodium without addition of the nanoparticles is similarly imaged, no bright pixels appear, which makes display on a graph impossible. If the brightness were displayed on FIG. 7, the line would be overlapped with the base line of the graph. It is possible to confirm from the graph in FIG. 7 that the ascending rate of the relative brightness in the emission area is extremely high in the case of the nanoparticle-dispersed sodium.

Fourth Embodiment

This fourth embodiment shows one embodiment in which the above-described brightness-enhancing phenomenon of the liquid fluid is utilized. This embodiment is for realization of an apparatus and a method for detecting a leak of nanoparticle-dispersed high-performance liquid sodium resulted from uniformly dispersing nanoparticles in liquid sodium as a coolant for fast breeder reactor.

Figure 8:
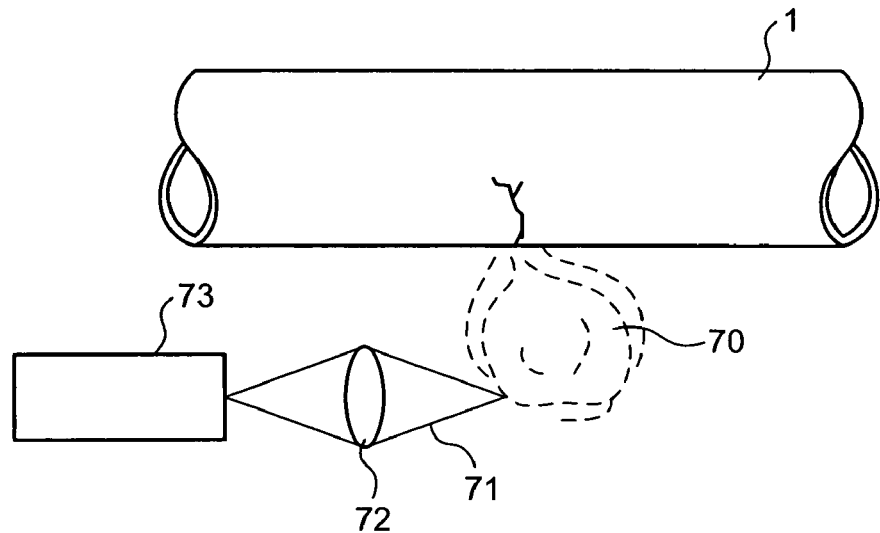
FIG. 8 is a diagram to explain a fourth embodiment of the present invention and is a schematic structural diagram representing a leak detection method for liquid fluid according to the present invention.
Figure 9:
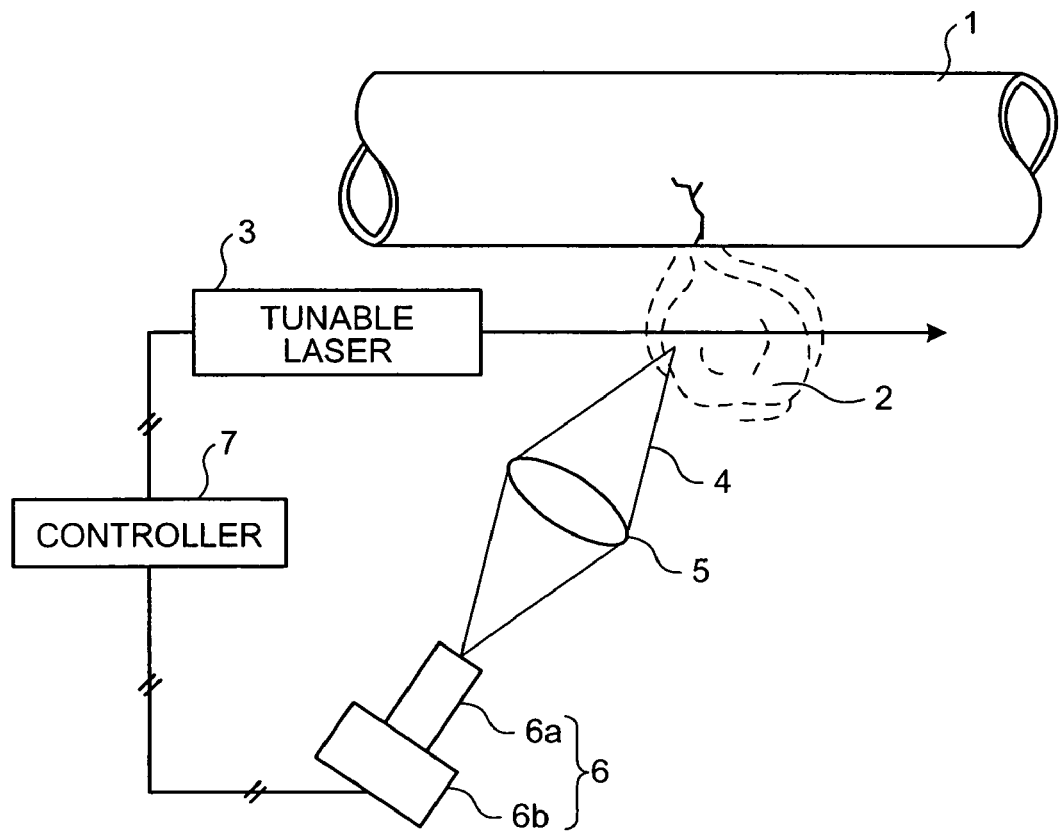
FIG. 9 is a schematic structural diagram representing a conventional leak detection method for liquid fluid.

This embodiment is explained with the use of FIG. 8. The same components shown as those shown in FIG. 9 are designated by the same numerals in the figure, thereby simplifying explanations. When a leak occurs caused by a crack or the like in the opaque wall 1 of the piping, the container, or the like, the leak is easily detected with a simple photodetector 73 by means of only measuring its emission 71 by simply condensing with a condenser lens 72 because the leaked nanoparticle-dispersed high-performance liquid sodium 70 emits with a brightness as high as naked eyes can confirm in the dark when the coolant inside is the nanoparticle-dispersed high-performance liquid sodium according to the present invention.

In this case, the brightness of the nanoparticle-dispersed high-performance sodium 70 has been enhanced without application of excitation energy such as laser beams from the outside. Thus, the surrounding atmosphere is in a normal state and not excited, and therefore no emission phenomenon occurs. That is, when emission can be confirmed at a measuring point, it means that the emission is caused only by the nanoparticle-dispersed high-performance sodium (vapor) 70. Accordingly, it is unnecessary to measure by setting time lag with a controller by making use of CCD imaging device with a shutter function, and it is possible to know in real time whether a leak occurs when the amount of light at a target point is instantly measured with the simple photodetector 73.

For the leak detector in this case, it can be composed of a simple photo detection system that is a combination of the condenser lens 72 and the simple photodetector 73, and therefore, it is possible to monitor a leak at low cost and in a small space.

INDUSTRIAL APPLICABILITY

As has been described hereinbefore, the nanoparticle-dispersed liquid fluid of the present invention is characterized in that no oxidized film exists on the surfaces of the nanoparticles in the base material of liquid fluid and the nanoparticles are uniformly dispersed in the base material of the liquid fluid. owing to the composition, it is possible to desirably enhance or suppress a property desired to be enhanced and a property desired to be suppressed among various specific properties possessed by a liquid fluid for a purpose of use. Therefore, according to the present invention, a high-performance alternative liquid fluid can be offered at low cost only by mixing and dispersing nanoparticles uniformly in a state of absence of oxidized films on the surfaces in a liquid fluid conventionally used in various industrial fields. Thus, the advantage of industrial applicability is enormous. Particularly when it is applied to a liquid fluid having a light-emitting property, its brightness of the light emission can be significantly enhanced, and a remarkable effect that detection of a leak of the liquid fluid, confirmation of its location (measurement of moving velocity and dispersion velocity, and the like), and the like become easy to be carried out is obtained.

The invention claimed is:

1. A production method to produce a nanoparticle-dispersed high-performance liquid fluid, comprising:

vaporizing and mixing together material of a liquid fluid and material of nanoparticle under an inert gas atmosphere to form a vaporized mixture;

separating a nanoparticle/fluid atom complex from other atomic constituents of the liquid fluid and the nanoparticles by means of issuing the vaporized mixture from a small hole under vacuum atmosphere depending on mass differences, the nanoparticle/fluid atom complex being in a form where constituting atoms of the material of the liquid fluid are adsorbed on the surfaces of the nanoparticles produced by the vaporization and mixing; and dispersing the separated nanoparticle/fluid atom complex in the liquid fluid, and the liquid fluid including a liquid fluid base material.

2. The production method according to claim 1, wherein the nanoparticle is at least one kind of ultrafine particle selected from a metal or a nonmetal.

3. The production method according to claim 1, wherein a particle size of the nanoparticle is not larger than 1000 nanometers in diameter.

4. The production method according to claim 1, wherein the performance enhancement is a reduction in specific reactivity possessed by the liquid fluid base material.

5. The production method according to claim 1, wherein the liquid fluid base material is liquid sodium.

6. The production method according to claim 5, wherein the performance enhancement is a reduction in reactivity to air or water possessed by the liquid fluid base material.

7. The production method according to claim 5, wherein the performance enhancement is a reduction in minute-crack penetration property possessed by the liquid fluid base material.

8. The production method according to claim 5, wherein the performance enhancement is an enhancement of a brightness of D-line emission specific to the liquid fluid base material.

* * * * *